United States Patent
Frasher et al.

(10) Patent No.: US 8,494,869 B1
(45) Date of Patent: Jul. 23, 2013

(54) METHOD AND SYSTEM FOR PRESENTING TREATMENT OPTIONS

(75) Inventors: Thomas Frasher, Sunnyvale, CA (US);
Todd Matthew Fitch, Santa Clara, CA (US); Steven A. Sholtis, El Dorado Hills, CA (US)

(73) Assignee: Intuit Inc., Mountain View, CA (US)

( * ) Notice: Subject to any disclaimer, the term of this patent is extended or adjusted under 35 U.S.C. 154(b) by 1068 days.

(21) Appl. No.: 11/830,818

(22) Filed: Jul. 30, 2007

(51) Int. Cl.
*G06Q 10/00* (2012.01)

(52) U.S. Cl.
USPC ........................................ 705/2; 705/3; 705/4

(58) Field of Classification Search
USPC ................. 705/2–4; 1/1; 434/236; 707/104.1
See application file for complete search history.

(56) References Cited

U.S. PATENT DOCUMENTS

| | | | |
|---|---|---|---|
| 6,283,761 B1 * | 9/2001 | Joao | 434/236 |
| 7,593,952 B2 * | 9/2009 | Soll et al. | 1/1 |
| 2002/0184050 A1 * | 12/2002 | Papageorge | 705/2 |
| 2003/0046113 A1 * | 3/2003 | Johnson et al. | 705/3 |
| 2007/0156455 A1 * | 7/2007 | Tarino et al. | 705/2 |
| 2007/0198296 A1 * | 8/2007 | Pellinat et al. | 705/2 |
| 2008/0215627 A1 * | 9/2008 | Higgins et al. | 707/104.1 |

* cited by examiner

*Primary Examiner* — Valerie Lubin
(74) *Attorney, Agent, or Firm* — Osha Liang LLP

(57) ABSTRACT

In general, the invention relates to a method for presenting a plurality of treatment options. The method includes obtaining medical information associated with an individual, wherein the medical information specifies an individual condition. The method further includes obtaining treatment information associated with the individual condition from a first plurality of benefit claims, generating the plurality of treatment options using the treatment information, and presenting the plurality of treatment options to a user.

35 Claims, 6 Drawing Sheets

US 8,494,869 B1

METHOD AND SYSTEM FOR PRESENTING TREATMENT OPTIONS

BACKGROUND

An individual may be interested in acquiring health care information. Specifically, an individual may be interested in obtaining information about medical treatments for a specific medical condition. For example, an individual that has contracted chicken pox may wish to seek out information related to the treatment of chicken pox.

Typically, an individual with a medical condition consults a doctor to diagnose the medical condition and receive treatment for the medical condition. Specifically, the doctor may diagnose the condition and recommend a number of treatment options to the individual, including a medical disclosure of the benefits and risks of each treatment option. At this stage, the individual may select a treatment based on the doctor's recommendation. A doctor's recommendation is typically based on his personal knowledge and experience as a medical professional. Further, the doctor may consult with other doctors or medical sources prior to making a recommendation to a patient.

Rather or in addition to consulting a doctor, an individual may perform his own investigation of the medical condition. The individual may search for medical information provided in a number of sources and formats. Specifically, the individual may consult a number of sources on the Internet or a local library regarding the medical condition. For example, after consulting a doctor, the individual may research the treatment option recommended by the doctor on the Internet or at a local library. The medical information provided by these Internet sources is typically based on information provided by medical professionals (e.g., doctors, nurses, pharmacists, or other medical professional).

SUMMARY

In general, in one aspect, the invention relates to a method for presenting a plurality of treatment options. The method includes obtaining medical information associated with an individual, wherein the medical information specifies an individual condition. The method further includes obtaining treatment information associated with the individual condition from a first plurality of benefit claims, generating the plurality of treatment options using the treatment information, and presenting the plurality of treatment options to a user.

In general, in one aspect, the invention relates to a method for presenting a plurality of treatment options. The method includes initiating a request for the plurality of treatment options, wherein the request specifies an individual condition associated with an individual based on which treatment information associated with a plurality of benefit claims is obtained. The method further includes viewing the plurality of treatment options, wherein the plurality of treatment options is generated based on the treatment information received in response to the request.

In general, in one aspect, the invention relates to a system for presenting a plurality of treatment options. The system includes a data interface configured to obtain a first plurality of benefit claims, a treatment analyzer configured to obtain treatment information for an individual condition from the first plurality of benefit claims and generate the plurality of treatment options for the individual condition using the treatment information, and a user interface configured to obtain medical information associated with an individual, wherein the medical information specifies the individual condition, and present the plurality of treatment options to a user.

In general, in one aspect, the invention relates to a computer readable medium, embodying instructions executable by the computer to perform method steps for presenting a plurality of treatment options, the instructions including functionality to obtain medical information associated with an individual, wherein the medical information specifies an individual condition. The instructions further include functionality to obtain treatment information associated with the individual condition from a first plurality of benefit claims, generate the plurality of treatment options using the treatment information, and present the plurality of treatment options to a use.

In general, in one aspect, the invention relates to a computer readable medium, embodying instructions executable by the computer to perform method steps for presenting a plurality of treatment options, the instructions including functionality to initiate a request for the plurality of treatment options, wherein the request specifies an individual condition associated with an individual based on which treatment information associated with a plurality of benefit claims is obtained. The instructions further include functionality to view the plurality of treatment options, wherein the plurality of treatment options is generated based on the treatment information received in response to the request.

Other aspects of the invention will be apparent from the following description and the appended claims.

DETAILED DESCRIPTION

Figure 1:
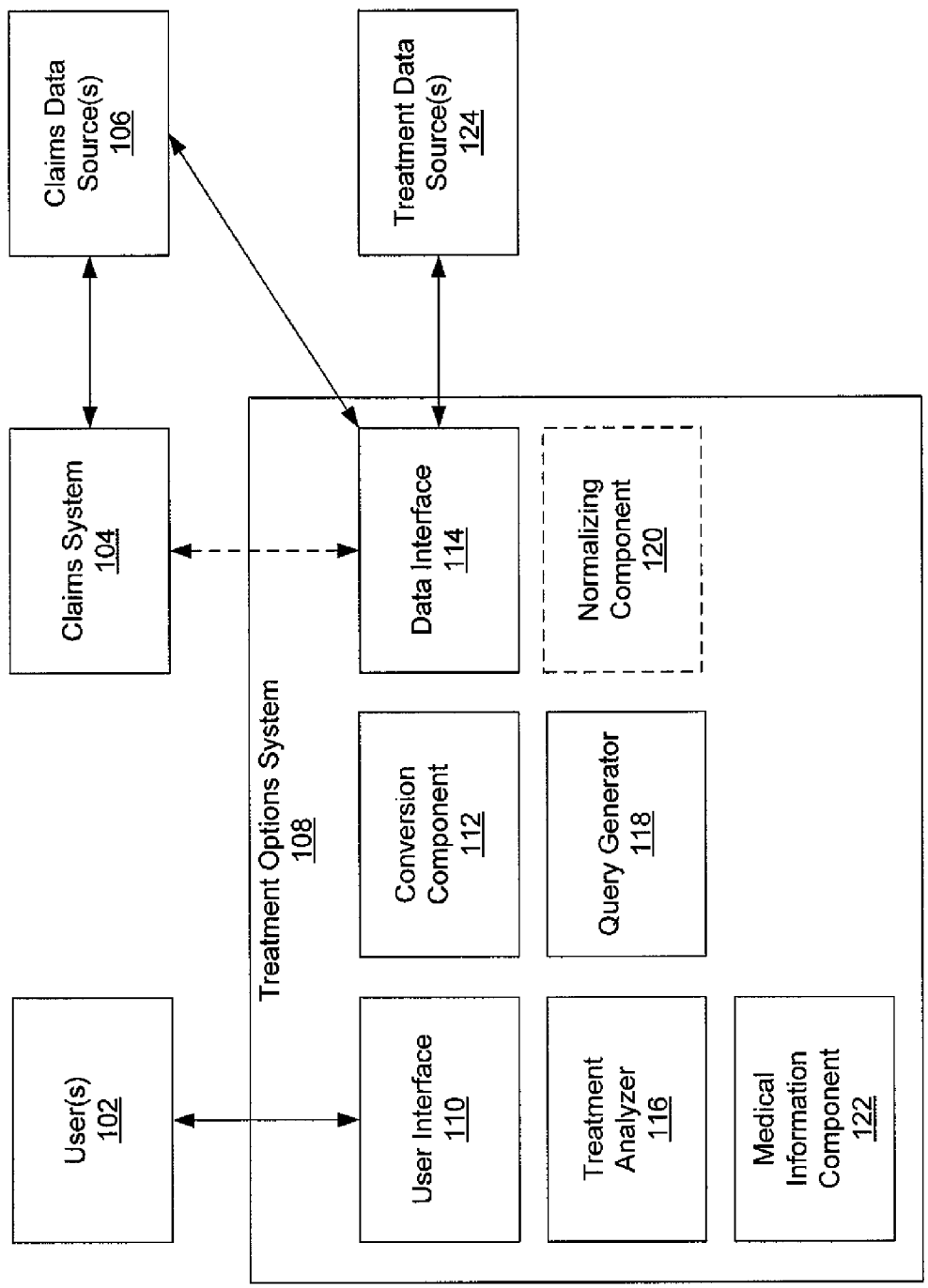
FIG. 1 shows a system in accordance with one or more embodiments of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid obscuring the invention. As used herein in the specification and figures, "ST" is essentially the same as "Step."

In general, embodiments of the invention relate to providing a method and a system for presenting treatment options to a user. More specifically, embodiments of the invention provide a method and system to present treatment options to a user based on treatment information, where the treatment information is obtained from benefit claims. The treatment options may include an effectiveness rating, which is calculated based on attributes associated with each of the treatment options.

FIG. 1 shows a system for presenting treatment options in accordance with one or more embodiments of the invention. The system includes user(s) (102) interacting with a treatment options system (TOS) (108) using a user interface (110). The TOS (108) further includes a conversion component (112), a data interface (114), a treatment analyzer (116), a query generator (118), and a medical information component (122). Optionally, the TOS (108) may further include a normalizing component (120). In one or more embodiments of the invention, the data interface (114) interacts with a claims data source(s) (106) and a treatment data source(s) (124). The claims data source(s) (106) interacts with a claims system (104). Optionally, the data interface (114) may interact with the claims system (104). Each of the aforementioned components is discussed below.

In one or more embodiments of the invention, each of the user(s) (102) may be a consumer of health care services. A consumer, as used herein, includes anyone that consumes health care services directly (e.g., a patient, employee, test subject, or other direct consumer of health care services) or indirectly (e.g., a health plan customer service representative, a medical professional, or other indirect consumer of health care services). In one or more embodiments of the invention, in the case where the user(s) (102) are an indirect consumer of health care services, the user(s) (102) may interact with the TOS (108) to request treatment options for an individual condition associated with an individual. An individual, as used herein, includes anyone that consumes health care services directly (e.g., a patient, employee, test subject, or other direct consumer of health care services).

In one or more embodiments of the invention, the user(s) (102) may interact with the user interface (110). For example, the user(s) (102) may access the user interface (110) over the Internet (or other Wide Area Network or Local Area Network) through a web browser (or other interface for communicating over a network). Alternatively, the user(s) (102) may interact with the user interface (110) through an application running natively on a user's (102) local computer (not shown). Further, in one or more embodiments of the invention, the user interface (110) may interact with the user(s) (102) through use of notifications. The notifications may be conveyed by electronic mail, short message service (SMS), or some other form of correspondence.

In one or more embodiments of the invention, the user interface (110) may be configured to receive requests for treatment options from the user(s). In one or more embodiments of the invention, the TOS (108) may be configured to process the requests. More specifically, the TOS (108) is configured to obtain the treatment options in response to the request and present the treatment options to the user(s) (102).

In one or more embodiments of the invention, the TOS (108) may be configured to store information in the treatment data source(s) (124) using a data interface (114). In one or more embodiments of the invention, the treatment data source(s) (124) is a data store (e.g., a database, a file system, one or more data structures configured in a memory, an extensible markup language (XML) file, some other medium for storing data, or any suitable combination thereof), which may include information (e.g., history of requests, personal information, and health care plan information) related to the user(s) (102).

In one or more embodiments of the invention, the query generator (118) may be configured to generate queries for retrieving information from the treatment data source(s) (124). Further, the query generator (118) may be configured to generate queries that aggregate data based on any number of attributes within the treatment data (e.g., diagnosis, claim procedure, service procedure, and/or other data). In one or more embodiments of the invention, the treatment data source(s) (124) may also include information associated with benefit claims and/or treatment options.

In one or more embodiments of the invention, benefit claims may be submitted by or on behalf of members (i.e., consumers who are covered under a health plan offered by a health plan provider) to one or more benefit plans included in a health plan provided by the health plan provider. For example, benefit claims may correspond to medical claims, dental claims, pharmacy claims, vision claims, or claims related to any other type of health services claim. In one or more embodiments of the invention, the claims system (104) may be configured to receive and process benefit claims. More specifically, the claims system (104) may be configured to store information associated with benefit claims in the claims data source(s) (106). In one or more embodiments of the invention, the claims data source(s) (124) is a data store(s) (e.g., a database, a file system, one or more data structures configured in a memory, an extensible markup language (XML) file, a medium for storing data, or any suitable combination thereof), which may include information related to the benefit claims (e.g., diagnosis, claim procedure, service date, service diagnosis, service procedure, or any related information).

In one or more embodiments of the invention, the data interface (114) may interact with the claims data source(s) (106). That is, the data interface (114) may be configured to retrieve benefit claims from the claims data source(s). In addition, in one or more embodiments of the invention, the query generator (118) may be configured to generate queries for retrieving benefit claims from the claims data source(s) (106). Further, a query may be configured to transform data associated with benefit claims to obtain attributes associated with treatment options (e.g., average duration, common symptoms, efficacy, or any other information associated with treatment options).

Alternatively, the retrieval of benefit claims may be accomplished without the use of the query generator (118). In such scenarios, a health care data transfer (HCDT) protocol, as described in U.S. patent application Ser. No. 11/799,170 entitled "METHOD AND SYSTEM FOR HEALTHCARE DATA EXCHANGE" and incorporated herein by reference in its entirety, may be used to retrieve benefit claims. More specifically, the data interface (114) may be configured to interact with the claim system (104) using the HCDT protocol. That is, in one or more embodiments of the invention, the data interface (114) may be configured to send a get request message for data corresponding to a health care topic (e.g., a provider topic, a medical claim topic, a medical service topic, a pharmacy claim topic, a benefit plans topic, or any other topic) to the claims system (104). Further, the data interface (114) may be configured to receive results in response to a get request message from the claims system (104). For example, benefit claims may be obtained as data corresponding to a medical claim topic and/or medical service topic.

In one or more embodiments of the invention, the health care topic for which data is to be retrieved is specified as one of the parameters of a get request message. In addition, search criteria may be specified as one of the parameters of a get request message. The search criteria may be used to further define the data for retrieval. For example, the search criteria may include an individual condition and specify that only data associated with the individual condition (e.g., treatment options for the individual condition) should be returned. Further, the action result in the response message (corresponding to a get request message) may be a data structure that includes the requested treatment data or an indication that the requested "get" action was not completed (e.g., an exception was thrown).

In one or more embodiments of the invention, an individual condition may correspond to a medical condition or disease diagnosed by a health care provider. Examples of individual conditions include, but are not limited to, asthma, cancer, a common cold, measles, a cavity, glaucoma, a pinched nerve, or some other medical condition or disease. Further, the health care provider may designate a prescribed treatment for the individual condition. Those skilled in the art will appreciate that the prescribed treatment may correspond to a medical service provided by the health care provider, a prescription for medication, an exercise regimen, a dietary restriction, various treatments, or any combination thereof.

Continuing with FIG. 1, in one or more embodiments of the invention, the conversion component (112) may be configured to process benefit claims to obtain treatment information. More specifically, the conversion component (112) may be configured to convert benefit claim codes to corresponding treatment information attributes. Benefit claim codes may include any code representing information related to a benefit claim (e.g., claim status code, facility code, diagnosis code, patient status code, etc.). In one or more embodiments of the invention, the conversion component (112) may be configured to convert benefit claim codes based on a health plan provider associated with the benefit claim. In this case, a health plan provider may utilize a set of benefit claim codes specific to the health plan provider.

More specifically, the conversion component (112) may be configured to convert benefit claim codes to benefit claim descriptions. For example, a claim status code may be converted to a claim status description to be included in treatment information. Those skilled in the art will appreciate that any number of benefit claim codes may be converted to be included in treatment information.

In one or more embodiments of the invention, the normalizing component (120) is configured to normalize benefit claims from multiple health plan providers. More specifically, the normalizing component (120) may alter benefit claims from multiple providers such that they use a common set of benefit claim codes. In this case, the benefit claims from multiple health plan providers may be stored in the treatment data source(s) (124) after converting each set of benefit claim codes to the common set of benefit claim codes. For example, multiple health plan providers may utilize separate benefit plan codes for the patient status code. Benefit claims from each health plan provider may be converted to a common set of patient status codes to be stored in the treatment data source(s) (124).

In one or more embodiments of the invention, the treatment analyzer (116) may be configured to generate treatment options based on treatment information. A treatment option may include, but is not limited to, a treatment, an efficacy associated with the treatment option, an average duration of the treatment option, common side effects of the treatment option, average cost of the treatment option, an effectiveness rating of the treatment option, or some other attribute associated with the treatment option. Efficacy associated with the treatment option may correspond to the rate of occurrence of a desired outcome associated with the treatment option. In one or more embodiments of the invention, the treatment analyzer (116) is configured to calculate an effectiveness rating based on other attributes of the treatment option (e.g., efficacy associated with the treatment option, average duration of the treatment option, common side-effects of the treatment option, average cost of the treatment option, or any other applicable information associated with the treatment option).

In one or more embodiments of the invention, the user interface (110) may be configured to present treatment options to the user(s) (102). In addition, the user interface (110) may be configured to identify one of the treatment options as the most appropriate for the user (or for an individual if the user is not a patient) based on the effectiveness of the treatment option. In one or more embodiments of the invention, the user interface (110) may be configured to allow the user(s) (102) to filter the treatment options presented. More specifically, the user interface (110) may be configured to allow a user to specify criteria for filtering treatment information used to obtain treatment options.

Alternatively, the criteria may be used by the query generator (118) to filter the benefit claims to be obtained. More specifically, the criteria may be used by the query generator (118) to generate queries for retrieving benefit claims from the claims data source(s) (106).

In one or more embodiments of the invention, the user interface (110) may be configured to accept medical information. The medical information may specify information (e.g., medical history, age, sex, weight, or any other medical information) associated with an individual having an individual condition. In one or more embodiments of the invention, the medical information component (122) may be configured to manage medical information. That is, the medical information component (122) may be configured to store medical information in the treatment data source(s) (124). In one or more embodiments of the invention, the medical information component (122) may be configured to specify portions of the medical information. In this case, the treatment analyzer (116) may be configured to use the specified portions of the medical information to filter treatment information. In addition, the medical information component (122) may be configured to extract medical information from benefit claims associated with the user(s) (102), for example, when the user(s) is the individual.

Figure 2:
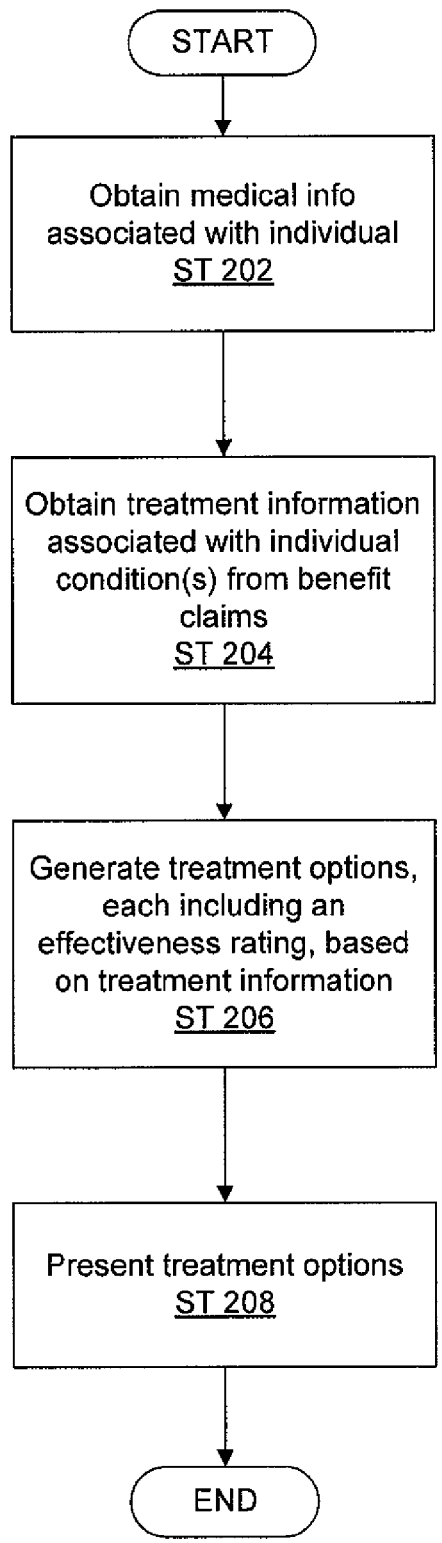
FIG. 2-5 shows flow charts in accordance with one or more embodiments of the invention.

FIG. 2 shows a flow chart for presenting treatment options in accordance with one or more embodiments of the invention. In one or more embodiments of the invention, one or more of the steps shown in FIG. 2 may be omitted, repeated, and/or performed in a different order than that shown in FIG. 2. Accordingly, the specific arrangement of steps shown in FIG. 2 should not be construed as limiting the scope of the invention.

In ST 202, medical information associated with an individual is obtained. In one or more embodiments of the invention, the medical information may include an individual condition. Those skilled in the art will appreciate that the medical information may further include, but is not limited to, a medical history, an age, a weight, a prescribed treatment, or some other information related to the individual. In one or more embodiments of the invention, the medical information may be obtained from benefit claims associated with the individual. Alternatively, the individual or some other party with the individual's permission (e.g., a guardian, a designated person, etc.) may provide the medical information.

Continuing with FIG. 2, treatment information associated with the individual condition may be obtained from benefit claims (ST 204). In one or more embodiments of the invention, the benefit claims are obtained directly from a claims data source. Alternatively, a "get" request message is sent to a server, which is operatively connected to the claims data source, to obtain the benefit claims. Additional details related to ST 204 are discussed in connection with FIG. 3.

At this stage, treatment options may be generated based on the treatment information (ST 206). In one or more embodiments of the invention, each treatment option may include an effectiveness rating. Those skilled in the art will appreciate that each treatment option may further include, but is not limited to, an average duration of the treatment option, an average cost of the treatment option, common side-effects of the treatment option, related treatment options, and/or other information related to the treatment option.

In one or more embodiments of the invention, the treatment options are presented (ST 208), for example, to a user. Further, one of the treatment options may be identified as having the highest relative effectiveness rating as compared with the other treatment options. More specifically, a treatment option with the highest relative effectiveness may be highlighted in the presentation of the treatment options. Further, in one or more embodiments of the invention, treatment options with an effectiveness rating less than a predefined threshold may be excluded from the presentation of the treatment options. Those skilled in the art will appreciate that treatment options may be excluded from the presentation of treatment options based on any number of predefined criteria (e.g., non-surgical procedure preference, holistic medicine preference, geographical region, health plan, or some other preference of the individual (or the user using system to determine treatment options for the individual)).

Figure 3:
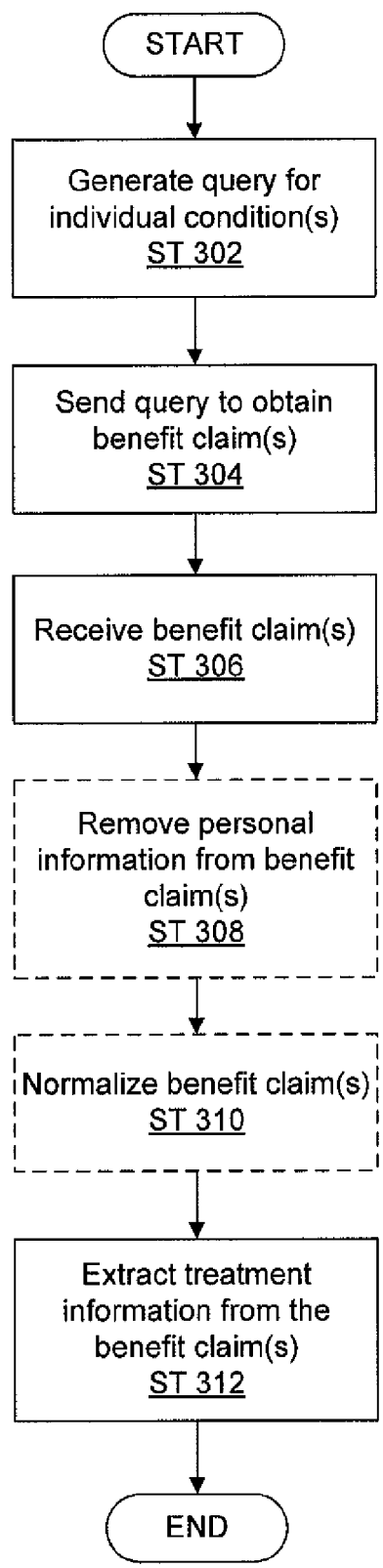

FIG. 3 shows a flow chart for obtaining treatment information in accordance with one or more embodiments of the invention. In one or more embodiments of the invention, one or more of the steps shown in FIG. 3 may be omitted, repeated, and/or performed in a different order than that shown in FIG. 3. Accordingly, the specific arrangement of steps shown in FIG. 3 should not be construed as limiting the scope of the invention.

In one or more embodiments of the invention, the treatment information may be obtained from benefit claims (in a similar manner to ST 204 in FIG. 2). The following describes one embodiment for a manner of obtaining treatment information from benefit claims. In ST 302, a query is generated for the individual condition(s). Those skilled in the art will appreciate that multiple queries may be generated to retrieve benefit claims from multiple data sources. In one or more embodiments of the invention, the query may specify criteria for limiting the benefit claims returned in response to the query. For example, criteria specified may include, but is not limited to, medical history, age, weight, health plan, geographic region, or some other information associated with the individual.

At this stage, the query is sent to obtain benefit claim(s) (ST 304). In one or more embodiments of the invention, the query may be sent to a claims data source including the benefit claim(s). Alternatively, the query may be sent to a server operatively connected to the claims data source, which includes the benefit claim(s). Alternatively, in the case of multiple claims data sources, multiple queries may be sent to claims data source(s) and/or server(s) operatively connected to claims data source(s).

In response to the query, the benefit claim(s) are received (ST 306). In one or more embodiments of the invention, the benefit claim(s) may correspond to benefit claim(s) associated with the individual condition. In addition, the benefit claim(s) may be filtered based on any number of criteria (e.g., age of individual, medical history of individual, weight of individual, etc.).

Optionally, personal information may be removed from the benefit claim(s) (ST 308). In one or more embodiments of the invention, the benefit claim(s) may include personal information associated with a member of a health plan. In this case, the personal information may be removed to protect the privacy of the member. In one or more embodiments of the invention, the personal information may be removed before the benefit claim(s) are received at ST 306. For example, a process executing on the claims data source (or a system providing access thereto) may remove the personal information prior to sending the benefit claim(s).

Continuing with the discussion of FIG. 3, optionally, the benefit claims may be normalized (ST 310). In one or more embodiments of the invention, the benefit claim(s) may be associated with multiple health plans, where each health plan has a different set of benefit claim codes. The benefit claims may be normalized to ensure the benefit claims share a common set of benefit claim codes.

In one or more embodiments of the invention, the treatment information may be extracted from the benefit claim(s) (ST 312). More specifically, attributes of treatment options may be identified in the benefit claim(s) and then extracted to obtain treatment information. Further, benefit claim codes in the extracted treatment information may be converted to treatment information attributes. For example, benefit claim codes for claim procedures may be converted to claim procedure descriptions.

Figure 4:
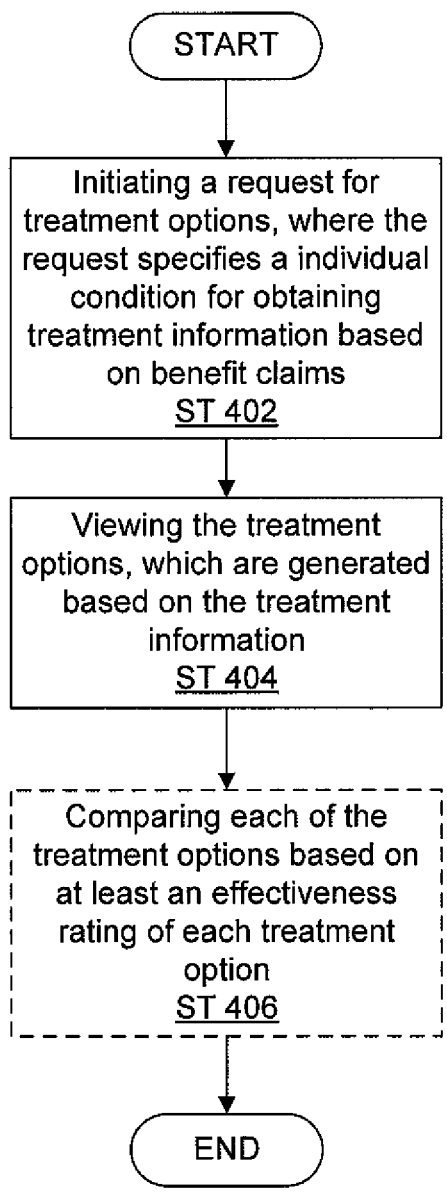

FIG. 4 shows a flow chart for obtaining treatment options in accordance with one or more embodiments of the invention. In one or more embodiments of the invention, one or more of the steps shown in FIG. 4 may be omitted, repeated, and/or performed in a different order than that shown in FIG. 4. Accordingly, the specific arrangement of steps shown in FIG. 4 should not be construed as limiting the scope of the invention.

In ST 402, a request is initiated for treatment options using a treatment options system (TOS). Those skilled in the art will appreciate that the TOS may be accessible from any number of locations (e.g. user's home, user's place of business, public terminal, or another other device capable of enabling the user to interact with the TOS). In one or more embodiments of the invention, the request may specify an individual condition for which treatment information is to be obtained. More specifically, the individual condition may be selected from a list of individual conditions. Those skilled in the art will appreciate that the request may further specify information such as, but not limited to, a medical history, a weight, an age, or some other information associated with the individual who has the individual condition.

In ST 404, the treatment options are viewed. In one or more embodiments of the invention, the treatment options may be viewed on a display. Alternatively, the treatment options may be received and viewed in a notification. Alternatively, the treatment options may be viewed on a print out and/or other forms of display.

Optionally, the treatment options may be compared based on the effectiveness rating of each treatment option (ST 406). In one or more embodiments of the invention, a treatment option with the highest relative effectiveness (as compared with the other treatment options for the individual condition) may be highlighted to facilitate comparison of the treatment options. Further, the treatment options may be arranged based on their effectiveness or some other attribute associated with the treatment options.

Figure 5:
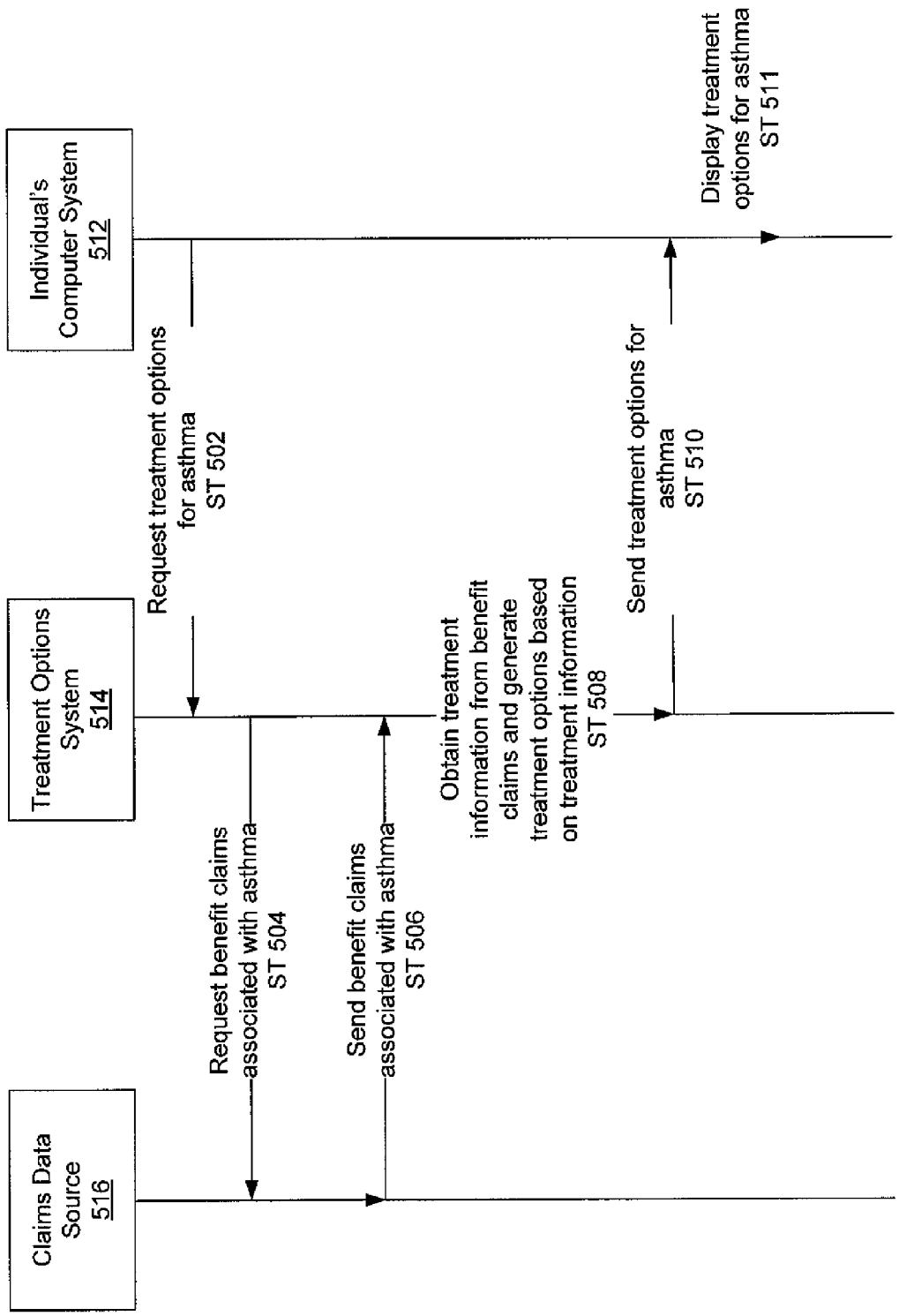

FIG. 5 shows a flow chart for obtaining treatment options in accordance with one or more embodiments of the invention. In one or more embodiments of the invention, one or more of the steps shown in FIG. 5 may be omitted, repeated, and/or performed in a different order than that shown in FIG. 5. Accordingly, the specific arrangement of steps shown in FIG. 5 should not be construed as limiting the scope of the invention.

The following discussion outlines an example of how an individual may use one or more embodiments of the treatment options system (TOS) described above. The example is not intended to limit the scope of the invention.

Turning to the example, assume there is an individual who has asthma and would like to investigate her potential treatment options. The individual may, via the individual computer system (512), interact with the TOS (514) to obtain treatment options.

In ST 502, the individual sends a request via the individual's computer system to the TOS (514) to obtain treatment options for asthma (i.e., the individual condition). In one or more embodiments of the invention, the individual may select asthma from a list of possible individual conditions. The TOS (514), upon receipt of the request, the TOS (514) requests benefit claims associated with asthma from a claims data source (516) (ST 504). In response to the request, the claims data source (516) sends the benefit claims associated with asthma to the TOS (514) (ST 506).

The TOS (514) extracts the treatment information from the benefit claims and then generates treatment options using the treatment information (ST 508). For example, the treatment options may include: Treatment Option A: bronchodilators administered via nebulizer with an effectiveness rating of 94 (out of 100); Treatment Option B: preventative medication with an effectiveness rating of 63 (out of 100); Treatment Option C: acupuncture with an effectiveness rating of 10 (out of 100); and Treatment Option D: homeopathy with an effectiveness rating of 55 (out of 100). Those skilled in the art will appreciate that an effectiveness rating may be calculated based on any number of scales (e.g., 1 to 10, 1 to 100, or some other scale).

The treatment options for asthma are then sent to the individual's computer system (ST 510). The treatments options are subsequently displayed on the individual's computer system (512) (ST 511). Though not shown in FIG. 5, the individual, via the individual's computer system (512) may also provide medical information. The medical information may then be used to: (i) limit the benefit claims received from the claims data source and, accordingly, provide treatment options more specific to the individual; (ii) limit the treatment options presented to the individual once the TOS (514) has generated the treatment options; and (iii) limit the treatment options presented to the individual once the individual's computer system has received the treatment options.

Figure 6:
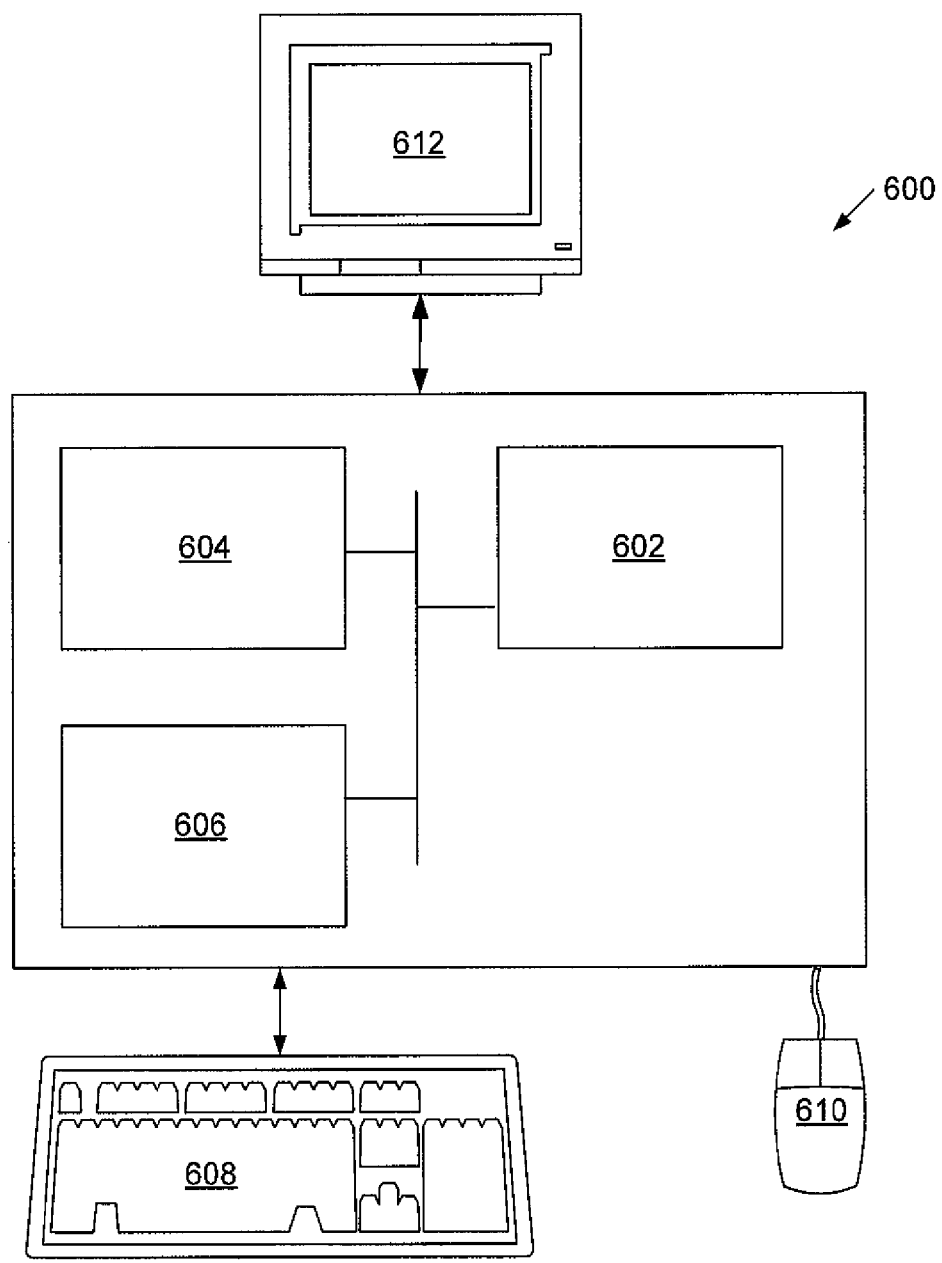
FIG. 6 shows a computer system in accordance with one or more embodiments of the invention.

The invention may be implemented on virtually any type of computer regardless of the platform being used. For example, as shown in FIG. 6, a networked computer system (600) includes a processor (602), associated memory (604), a storage device (606), and numerous other elements and functionalities typical of today's computers (not shown). The networked computer (600) may also include input means, such as a keyboard (608) and a mouse (610), and output means, such as a monitor (612). The networked computer system (600) is connected to a local area network (LAN) or a wide area network (e.g., the Internet) (not shown) via a network interface connection (not shown). Those skilled in the art will appreciate that these input and output means may take other forms, now known or later developed. Further, those skilled in the art will appreciate that one or more elements of the aforementioned computer (600) may be located at a remote location and connected to the other elements over a network.

Further, the invention may be implemented on a distributed system having a plurality of nodes, where each portion of the invention may be located on a different node within the distributed system. In one or more embodiments of the invention, the node corresponds to a computer system. Alternatively, the node may correspond to a processor with associated physical memory.

In one or more embodiments of the invention, software instructions to perform embodiments of the invention, when executed by a processor, may be stored on a computer readable medium such as a compact disc (CD), a diskette, a tape, a file, or any other computer readable storage device. Further, one or more embodiments of the invention may be implemented as an Application Program Interface (API) executing on a computer system(s), where the API includes one or more software instructions.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for presenting a first and second medical treatment options, comprising:

obtaining, using a processor, medical information associated with an individual, wherein the medical information specifies an individual condition;

obtaining, using the processor, medical treatment information associated with the individual condition from a first benefit claim and a second benefit claim, by:

sending a first benefit claims query to a first claims data source, specifying the individual condition, to obtain a first benefit claim from a first health plan provider, sending a second benefit claims query to a second claims data source, specifying the individual condition, to obtain a second benefit claim from a second health plan provider, receiving the first benefit claim in response to the first benefit claims query, wherein the first benefit claim is associated with a first benefit claim code set, receiving the second benefit claim in response to the second benefit claims query, wherein the first benefit claim and the second benefit claim are each associated with the individual condition and comprises the medical treatment information, and wherein the second benefit claim is associated with a second benefit claim code set, normalizing the first benefit claim using the first benefit claim code set to obtain a first normalized benefit claim, wherein the first benefit claim code set is associated with the first health plan provider, normalizing the second benefit claim using the second benefit claim code set to obtain a second normalized benefit claim, wherein the second benefit claim code set is associated with the second health plan provider, and extracting, using the processor, the medical treatment information from the first normalized benefit claim and the second normalized benefit claim;

identifying, using the processor, the first and second medical treatment options using the medical treatment information, wherein the first medical treatment option comprises a medical procedure, and wherein the second medical treatment option comprises an alternative medical treatment;

calculating a first effectiveness rating for the first medical treatment option;

calculating a second effectiveness rating for the second medical treatment option; and presenting the first and second medical treatment options and the first and second effectiveness ratings to a user.

2. The method of claim 1, further comprising:
identifying one of the first and second medical treatment options, wherein the one of the first and second medical treatment options is calculated to have a relatively higher effectiveness rating than a prescribed treatment associated with the individual.

3. The method of claim 2, wherein the medical information further comprises the prescribed treatment.

4. The method of claim 1, wherein each effectiveness rating of the first and second effectiveness ratings is calculated based on at least one attribute, wherein the attribute is associated with the first treatment option and selected from a group consisting of mortality rate, relapse rate, average cost, average duration, related treatments, common side effects, and efficacy.

5. The method of claim 4, wherein the at least one attribute is obtained from the first normalized benefit claim.

6. The method of claim 1, further comprising:
identifying one of the first and second medical treatment options based on a medical history associated with the individual.

7. The method of claim 1, wherein the benefit claims query further specifies a medical history associated with the individual.

8. The method of claim 1, wherein identifying the first and second medical treatment options comprises:
obtaining a subset of the medical treatment information based on a medical history associated with the individual; and
extracting the first and second medical treatment options from the subset of the medical treatment information.

9. The method of claim 8, wherein the medical history associated with the individual is obtained from a third benefit claim.

10. The method of claim 1, wherein obtaining the medical information comprises:
receiving a request from the user for the first and second medical treatment options; and
extracting the medical information from the request, wherein the medical information is associated with the individual.

11. The method of claim 1, wherein the medical information comprises a medical history associated with the individual.

12. The method of claim 1, wherein the user is one selected from a group consisting of a health plan customer service representative and a medical professional.

13. The method of claim 1, wherein the individual corresponds to the user.

14. The method of claim 1, wherein the first benefit claim is obtained from one of a plurality of health plans.

15. The method of claim 1, wherein the first benefit claim is associated with a health plan, wherein the individual is associated the health plan.

16. A method for presenting a first and second medical treatment options, comprising:
initiating, using a processor, a request for the first and second medical treatment options, wherein the request specifies an individual condition associated with an individual; and
viewing the first and second medical treatment options and a first and second effectiveness ratings,
wherein the first and second medical treatment options are identified using medical treatment information obtained in response to the request, wherein the first medical treatment option comprises a medical procedure, wherein the second medical treatment option comprises an alternative medical treatment, wherein the first and second effectiveness ratings are calculated for the first and second medical treatment options, and wherein the medical treatment information is obtained using the processor by:
obtaining, using a first benefit claims query specifying the individual condition, a first benefit claim associated with the individual condition and comprising the medical treatment information, wherein the first benefit claim is associated with a first benefit claim code set,
obtaining, using a second benefit claims query specifying the individual condition, a second benefit claim associated with the individual condition and comprising the medical treatment information, wherein the second benefit claim is associated with a second benefit claim code set,
normalizing the first benefit claim using the first benefit claim code set to obtain a first normalized benefit claim, wherein the first benefit claim code set is associated with a first health plan provider,
normalizing the second benefit claim using the second benefit claim code set to obtain a second normalized benefit claim, wherein the second benefit claim code set is associated with a second health plan provider, and
extracting the medical treatment information from the first normalized benefit claim and the second normalized benefit claim.

17. The method of claim 16, further comprising:
comparing the first and second medical treatment options based on at least the first and second effectiveness ratings.

18. The method of claim 16, wherein one of the first and second medical treatment options is identified as having a relatively higher effectiveness rating than a prescribed treatment associated with the individual.

19. The method of claim 16, wherein each effectiveness rating of the first and second effectiveness ratings is calculated based on at least one attribute, wherein the at least one attribute is associated with the first and second medical treatment options and selected from a group consisting of mortality rate, relapse rate, average cost, average duration, related treatments, common side effects, and efficacy.

20. The method of claim 19, wherein the at least one attribute is obtained from the first normalized benefit claim.

21. The method of claim 16, wherein the request further specifies a medical history of the individual.

22. The method of claim 16, wherein the request further specifies a prescribed treatment for the individual.

23. The method of claim 16, wherein the request is initiated by one selected from a group consisting of the individual, a health plan customer service representative, and a medical professional.

24. The method of claim 16, wherein the first benefit claim is obtained from one of a health plans.

25. The method of claim 16, wherein the first benefit claim is associated with a health plan, wherein the individual is associated with the health plan.

26. A system for presenting a first and second medical treatment options, comprising:
a processor;
a data interface configured to obtain a first benefit claim and a second benefit claim;
a treatment analyzer executing on the processor and configured to:
obtain medical treatment information for an individual condition from the first benefit claim and the second benefit claim, by:
sending a first benefit claims query to a first claims data source, specifying the individual condition, to obtain the first benefit claim from a first health plan provider,
sending a second benefit claims query to a second claims data source, specifying the individual condition, to obtain the second benefit claim from a second health plan provider,
receiving the first benefit claim in response to the first benefit claims query, wherein the first benefit claim is associated with a first benefit claim code set,
receiving the second benefit claim in response to the second benefit claims query, wherein the first benefit claim and the second benefit claim are each associated with the individual condition and comprises the treatment information, wherein the second benefit claim is associated with a second benefit claim code set,
normalizing the first benefit claim using the first benefit claim code set to obtain a first normalized benefit claim, wherein the first benefit claim code set is associated with the first health plan provider,
normalizing the second benefit claim using the second benefit claim code set to obtain a second normalized benefit claim, wherein the second benefit claim code set is associated with the second health plan provider, and
extracting the medical treatment information from the first normalized benefit claim and the second normalized benefit claim;
identify the first and second medical treatment options for the individual condition using the medical treatment information, wherein the first medical treatment option comprises a medical procedure, and wherein the second medical treatment option comprises an alternative medical treatment;
calculate a first effectiveness rating for the first medical treatment option; and
calculate a second effectiveness rating for the second medical treatment option; and a user interface configured to:
obtain medical information associated with an individual, wherein the medical information specifies the individual condition; and
present the first and second medical treatment options and the first and second effectiveness ratings to a user.

27. The system of claim 26, further comprising:
a query generator configured to generate the first benefit claims query.

28. The system of claim 27, wherein the user interface is further configured to identify one of the first and second medical treatment options, wherein the one of the first and second medical treatment options is identified as having a relatively higher effectiveness rating than a prescribed treatment associated with the individual.

29. The system of claim 28, wherein the medical information further comprises the prescribed treatment.

30. The system of claim 28, wherein each effectiveness rating of the first and second effectiveness ratings is calculated based on at least one attribute, wherein the attribute is associated with the first and second medical treatment options and selected from a group consisting of mortality rate, relapse rate, average cost, average duration, related treatments, common side effects, and efficacy.

31. The system of claim 30, wherein the at least one attribute is obtained from the first normalized benefit claim and the second normalized benefit claim.

32. The system of claim 26, wherein the treatment analyzer is further configured to identify one of the first and second medical treatment options based on a medical history associated with the individual.

33. The system of claim 26, wherein the first benefit claims query further specifies a medical history associated with the individual.

34. A non-transitory computer readable medium, embodying instructions executable by the computer to perform method steps for presenting a first and second medical treatment options, the instructions comprising functionality to:
obtain medical information associated with an individual, wherein the medical information specifies an individual condition;
obtain medical treatment information associated with the individual condition from a first benefit claim and a second benefit claim, by:
sending a first benefit claims query to a first claims data source, specifying the individual condition, to obtain the first benefit claim from a first health plan provider,
sending a second benefit claims query to a second claims data source, specifying the individual condition, to obtain a second benefit claim from a second health plan provider,
receiving the first benefit claim in response to the first benefit claims query, wherein the first benefit claim is associated with a first benefit claim code set,
receiving the second benefit claim in response to the second benefit claims query, wherein the first benefit claim and the second benefit claim are each associated with the individual condition and comprises treatment information, and wherein the second benefit claim is associated with a second benefit claim code set,
normalizing the first benefit claim using the first benefit claim code set to obtain a first normalized benefit claim, wherein the first benefit claim code set is associated with the first health plan provider,
normalizing the second benefit claim using the second benefit claim code set to obtain a second normalized benefit claim, wherein the second benefit claim code set is associated with the second health plan provider, and
extracting the medical treatment information from the first normalized benefit claim and the second normalized benefit claim;
identify the first and second medical treatment options using the medical treatment information, wherein the first medical treatment option comprises a medical procedure, and wherein the second medical treatment option comprises an alternative medical treatment;
calculate a first effectiveness rating for the first medical treatment option;
calculate a second effectiveness rating for the second medical treatment option; and
present the first and second medical treatment options and the first and second effectiveness ratings to a user.

35. A non-transitory computer readable medium, embodying instructions executable by the computer to perform method steps for presenting a first and second medical treatment options, the instructions comprising functionality to:
- initiate a request for the first and second medical treatment options, wherein the request specifies an individual condition associated with an individual; and
- view the first and second medical treatment options and a first and second effectiveness ratings,
- wherein the first and second medical treatment options are identified using medical treatment information obtained in response to the request,
- wherein the first medical treatment option comprises a medical procedure,
- wherein the second medical treatment option comprises an alternative medical treatment,
- wherein the first and second effectiveness ratings are calculated for the first and second medical treatment options, and
- wherein the medical treatment information is obtained by:
  - obtaining, using a first benefit claims query specifying the individual condition, a first benefit claim associated with the individual condition and comprising the medical treatment information, wherein the first benefit claim is associated with a first benefit claim code set,
  - obtaining, using a second benefit claims query specifying the individual condition, a second benefit claim associated with the individual condition and comprising the medical treatment information, wherein the second benefit claim is associated with a second benefit claim code set,
- normalizing the first benefit claim using the first benefit claim code set to obtain a first normalized benefit claim, wherein the first benefit claim code set is associated with a first health plan provider,
- normalizing the second benefit claim using the second benefit claim code set to obtain a second normalized benefit claim, wherein the second benefit claim code set is associated with a second health plan provider, and
- extracting the medical treatment information from the first normalized benefit claim and the second normalized benefit claim.

\* \* \* \* \*